United States Patent [19]
Wada

[11] 3,942,360
[45] Mar. 9, 1976

[54] METHOD AND APPARATUS FOR MEASURING THE DEGREE OF CONTAMINATION OF LIQUIDS

[75] Inventor: Yoneji Wada, Fukuoka, Japan

[73] Assignee: Toshiba Kikai Kabushiki Kaisha, Tokyo, Japan

[22] Filed: Mar. 11, 1974

[21] Appl. No.: 450,245

[52] U.S. Cl. .............. 73/61 R; 73/432 PS; 356/70; 356/212
[51] Int. Cl.[2] .......................................... G01N 15/00
[58] Field of Search ............... 73/61 R, 53, 432 PS; 356/70, 212; 210/323 R, 335, 337; 209/237, 268, 355

[56] References Cited
UNITED STATES PATENTS

| | | | |
|---|---|---|---|
| 2,152,645 | 4/1939 | Holven et al. | 356/70 X |
| 2,273,356 | 2/1942 | Holven et al. | 356/212 X |
| 3,063,289 | 11/1962 | Moul | 73/61 R |
| 3,352,197 | 11/1967 | Porges et al. | 73/53 X |
| 3,521,750 | 7/1970 | Hamilton | 209/237 |
| 3,668,925 | 6/1972 | Mesek | 73/61 R |
| 3,756,400 | 9/1973 | Kammori | 209/237 X |

Primary Examiner—Richard C. Queisser
Assistant Examiner—Joseph W. Roskos
Attorney, Agent, or Firm—Wenderoth, Lind & Ponack

[57] ABSTRACT

Liquid containing contaminants is passed through a lamination of a plurality of filter papers and the quantities of the contaminants deposited on upper and lower filter papers are compared with each other to determine the degree of contamination of the liquid.

1 Claim, 3 Drawing Figures

METHOD AND APPARATUS FOR MEASURING THE DEGREE OF CONTAMINATION OF LIQUIDS

BACKGROND OF THE INVENTION

This invention relates to a method and apparatus for measuring the degree of contamination of liquids, and more particularly to a method and apparatus wherein fine contaminants contained in liquids such as oil utilized in hydraulic actuators, lubricating oil or the like are accumulated on filter papers for determining the degree of contamination.

Such oils are contaminated by foreign matters during their preparation, storage and use. Such contamination causes troubles in precise hydraulic actuators or bearings. Accordingly, it is necessary to measure the degree of contamination of such liquids before or during use thereof in order to know whether the liquids are clean liquids containing contamitants of less than a permissible limit. However, strict control of the degree of contamination of such liquids is usually ignored except in certain field of application.

In the United States of America, with the advance of space navigation engineering, a number of regulations have been established in connection with the degree of purity of liquids, and in Japan some of these regulations have been adopted in certain industries. However, as these regulations require special apparatus and highly trained engineers they are troublesome and uneconomical. Moreover, the methods specified in these regulations make possible a large error if the condition of measuring the degree of contamination of the liquid is not suitable, and such methods lack reproduceability so that in certain cases errors within ±33% are permitted.

In addition to the advance in space navigation engineering, techniques of a high degree of accuracy have been developed in other fields of engineering, so that it is necessary to control with the same degree of accuracy the quality of the liquids, such as oils utilized to operate various hydraulic actuators and bearing oils used in such fields. To meet such requirements a number of simple methods have been proposed for measuring the purity of liquids. Among these methods, a method wherein light is projected upon a liquid to be examined for causing the light to transmit through or be reflected by the liquid so as to determine the degree of contamination of the liquid in accordance with the quantity of light transmitted or reflected is used most widely. However, with this method, it is extremely difficult to accurately determine the degree of contamination because of the difference in the color of the liquid, change of the liquid color during measurement, variation in the color caused by the presence of contaminants and the coloring of the liquid. For example, the operator often is given an illusion that the liquid under measurement contains a large quantity of cntaminants due to the coloring of the liquid even when the liquid actually contains only a small quantity of the contaminants.

SUMMARY OF THE INVENTION

Accordingly, it is an object of this invention to provide a novel method and apparatus for enabling an unskilled operator to rapidly and accurately determine the degree of contamination of liquids without the difficulties described above.

Another object of this invention is to provide a novel method and apparatus for determining the degree of contamination of liquids which is not affected by the color of the liquids.

Still another object of this invention is to provide a novel method and apparatus capable of determining not only the concentration of the contaminants but also the particle size or particle size distribution of the contaminants.

Yet another object of this invention is to provide an improved apparatus for measuring the degree of contamination of liquids without errors caused by the difference in the characteristics of elements utilized to fabricate the apparatus.

According to one aspect of this invention there is provided a method of measuring the degree of contamination of liquids, characterized in that a liquid containing contaminants is filtered by passing it through a lamination of a plurality of filter papers and that the quantities of the contaminants deposited on the upper and lower filter papers are compared with each other thereby measuring the degree of contamination of the liquid.

According to another aspect of this invention there is provided apparatus for measuring the degree of contamination of liquids, characterized by comprising a filter including a container for receiving a definite quantity of a liquid containing contaminants, a lamination of a plurality of filter papers contained in the container, and a measuring device including a source of light for irradiating upper and lower filter papers taken out of the filter with light having a definite wavelength, photoelectric converting elements responsive to the light reflected by the upper and lower filter papers, respectively, for producing electric signals proportional to the quantities of the contaminants deposited on the upper and lower filter papers, respectively, and a bridge circuit for comparing the electric signals with each other, thus producing a differential output signal corresponding to the degree of contamination of the liquid.

Where the lamination comprises a plurality of filter papers having a different pore size in which the pore size decreases from the upper to the lower, it is possible to determine not only the concentration but also the particle size and particle size distribution of the contaminants.

BRIEF DESCRIPTION OF THE DRAWINGS

In the accompanying drawings.

DESCRIPTION OF THE PREFERRED EMBODIMENTS

Figure 1:
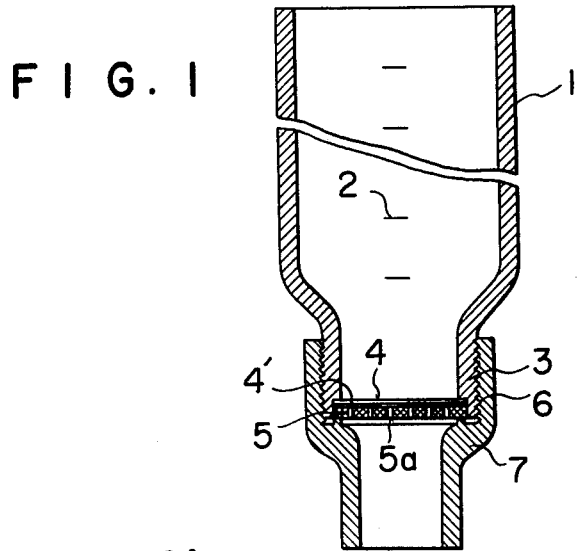
FIG. 1 shows a longitudinal section of a filter utilized in this invention.

FIG. 1 of the accompanying drawings shows a filter comprising a cylindrical container 1 made of a material which will not be dissolved by or not chemically react with the liquid to be measured, such as synthetic resins, polyethylene, polypropylene, polyvinyl chloride, glass, etc. A scale 2 is provided on the outer surface of the container 1 to indicate the quantity of the liquid contained therein. The upper end of the container 1 is open and a neck 3 having an inner diameter a little smaller than the filter paper to be used is provided at the lower end. A plurality of sheets of filter paper is inserted into the neck 3 through the lower opening of the container. According to this invention, at least two sheets 4 and 4" of the filter paper are inserted in a superposed relation and a protective disc 5 provided with a plurality of small perforations 5a is disposed below the stack of sheets of filter paper for supporting them when pressure or suction is applied for filtering. Screw threads 6 are formed on the outer surface of the neck 3 to receive a cylindrical cap 7 which is used to clamp the periphery of the sheets of filter paper between a shoulder formed at the lower end of the neck 3 and the protective disc 5.

Before using the container 1, it is washed with clean water to remove any residual contaminant and then dried. A definite quantity of the liquid to be measured is then put in the container and filtered by being passed through the filter paper by pressure suction which is applied through the cylindrical cap 7. After completing the filtering operation, the sheet of filter paper are removed by removing the cap 7 and the protective disc 5 and the condition of the upper filter paper 4 is compared with that of the lower filter paper 4'. It will be clear that most of the contaminant is deposited on the upper sheet of filter paper 4 so that it is possible to determine the quantity of contaminant or the degree of contamination by comparing the conditions of the upper and lower sheets of filter paper.

Figure 2:
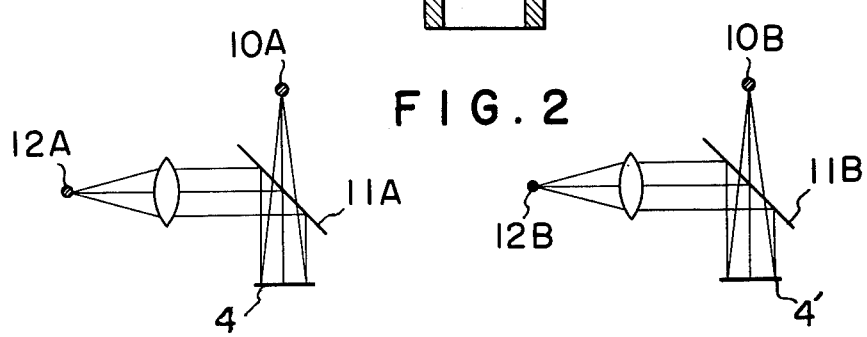
FIG. 2 is a diagrammatic representation for an optical device utilized in the measuring apparatus and
FIG. 3 is a circuit diagram of a bridge circuit utilized in combination with the optical device shown in FIG. 2.
Figure 3:
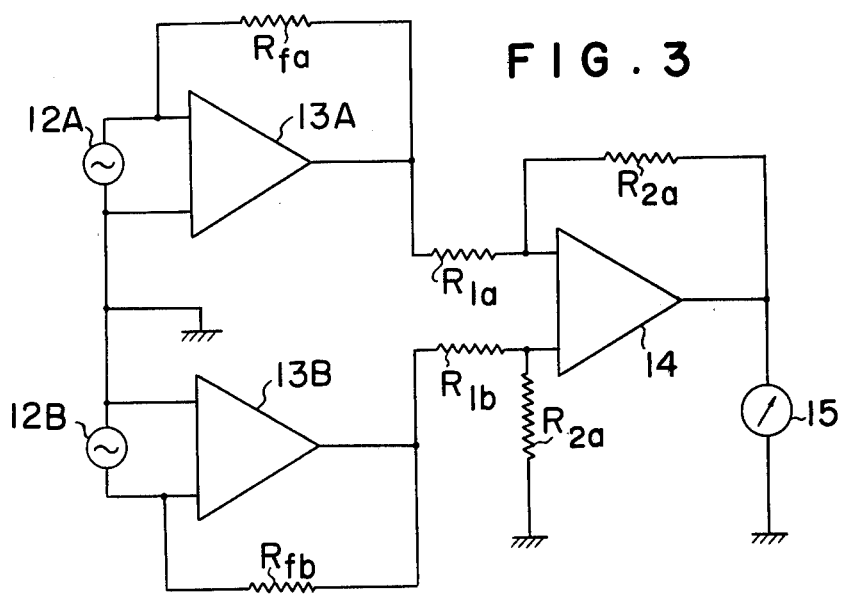

FIGS. 2 and 3 show apparatus suitable for this purpose. More particularly, as shown in FIG. 2, the upper and lower sheets of filter paper 4 and 4' are illuminated with monochromatic directional light having a wavelength of 7,000A and generated by light sources, for example luminous diodes 10A and 10B through semi-transparent reflective mirrors 11A and 11B. The light reflected by the sheets of filter paper 4 and 4' are reflected by reflective mirrors 11A and 11B toward photoelectric converting elements 12A and 12B to generate electric signals directly proportional to the quantities of the contaminants deposited on the upper and lower sheets of filter paper. The photoelectric converting elements may be solar cells, for example. The outputs from the photoelectric converting elements 12A and 12B are amplified by operational amplifiers 13A and 13B, and the outputs thereof are applied to a bridge circuit including resistors $R_{1a}$, $R_{1b}$, $R_{2a}$, $R_{2b}$, $R_{fa}$ and $R_{fb}$, and an operational amplifier 14. The output of operational amplifier 14 is applied to an indicating meter 15.

Before measurement, two standard sheets of filter paper (not yet used) are substituted for the sheets of filter paper 4 and 4' shown in FIG. 3. If there is any difference between the characteristics of the light sources 10A, 10B and photoelectric converting elements 12A, 12B and when the bridge circuit is not perfectly balanced, the bridge will produce a differential output. Then, one or both of the feedback resistors $R_{fa}$, $R_{fb}$ associated with amplifiers 13A and 13B are adjusted to perfectly balance the bridge. Then, sheets of filter paper 4 and 4' are substituted for the standard filter paper sheets. The output of the bridge circuit under these conditions is proportional to the quantity of the contaminants contained in the liquid because most of the contaminants deposits on the upper sheet of filter paper 4 and because upper and lower sheets are colored to the same degree by the liquid. Thus, even when the liquid is colored, its color does not affect in any way the result of measurement and the output from the bridge circuit is directly proportional to the quantity of the contaminants deposited on the upper sheets of filter paper or the difference between the quantities of the contaminants deposited on the upper and lower sheets of filter paper, or the concentration of the contaminants contained in the liquid.

Filter paper made of any suitable material can be used in this invention but it has been found that filter paper made of cellulose ester is suitable. However, filter paper for use in chemical analysis are also satisfactory. The pore size of the filter paper may range from 0.45 to 3.0 microns.

The comparison of the conditions of the two sheets of filter paper can also be made by visual inspection or with a microscope. If three or more sheets of filter paper having different pore sizes are laminated with that having the largest pore size positioned upper most, it is possible to determine not only the quantity of the contaminants but also the particle size or particle size distribution of the contaminants.

With the method of this invention it is possible to limit the permissible error to less than 5%.

While the filter illustrated in FIG. 1 is of the vertical type, it should be understood that it is also possible to use a horizontal type filter, so that the term "upper sheet filter paper" used herein means the sheet of filter paper through which the liquid is first passed.

I claim:

1. Apparatus for measuring the degree of contamination of liquids comprising a filter having a container for accommodating a definite volume of a liquid containing contaminants and a stack of a plurality of sheets of filter paper contained in said container, the pore size of said sheets of filter paper decreasing from the first to succeeding sheets in the direction in which the liquid passes therethrough; and a measuring device having a source of light having a definite wavelength and directed against the first and succeeding sheets of filter paper respectively having contaminants with different particle sizes thereon and which have been removed from said filter for irradiating said sheets, photoelectric converting elements positioned to receive light reflected from said sheets of filter paper and responsive to the light reflected by said first and succeeding sheets of filter paper respectively for producing electric signals proportional to the quantities of the contaminants deposited on said first and succeeding sheets of filter paper respectively, and a bridge circuit connected to said converting elements for comparing said electric signals with each other and producing a differential output signal corresponding to the concentration and the particle size of said contaminants.

* * * * *